United States Patent
Boaz

(10) Patent No.: US 8,329,938 B2
(45) Date of Patent: Dec. 11, 2012

(54) HYDROXYALKANOIC ACID AND HYDROXYALKANOICE ACID OLIGOMER ESTERS OF RETINOL

(75) Inventor: Neil Warren Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 13/031,375

(22) Filed: Feb. 21, 2011

(65) Prior Publication Data

US 2012/0215024 A1    Aug. 23, 2012

(51) Int. Cl.
  *C07C 69/66* (2006.01)
  *C07C 69/74* (2006.01)
  *C07C 69/34* (2006.01)
  *A61K 8/02* (2006.01)

(52) U.S. Cl. ......... 560/188; 560/128; 560/190; 424/401

(58) Field of Classification Search ........................ None
See application file for complete search history.

(56) References Cited

U.S. PATENT DOCUMENTS

| | | | |
|---|---|---|---|
| 4,107,290 A | 8/1978 | Jacquet et al. | |
| 5,605,933 A * | 2/1997 | Duffy et al. | 514/557 |
| 5,972,323 A * | 10/1999 | Lang et al. | 424/70.28 |
| 6,572,882 B1 | 6/2003 | Vercauteren et al. | |
| 7,030,265 B2 * | 4/2006 | Sin et al. | 560/129 |
| 7,098,246 B2 | 8/2006 | Geelings et al. | |
| 7,102,019 B2 | 9/2006 | Streicher et al. | |
| 7,670,606 B2 * | 3/2010 | Volkmann | 424/184.1 |
| 7,671,009 B2 * | 3/2010 | Ludin et al. | 514/1.1 |
| 8,029,810 B2 * | 10/2011 | Skold | 424/400 |
| 2003/0225160 A1 | 12/2003 | Geerlings et al. | |
| 2005/0015058 A1 | 1/2005 | Millerd | |
| 2005/0095232 A1 | 5/2005 | Volkmann | |
| 2009/0035236 A1 | 2/2009 | Maes et al. | |
| 2009/0035237 A1 | 2/2009 | Maes et al. | |
| 2009/0035240 A1 | 2/2009 | Maes et al. | |
| 2009/0035242 A1 | 2/2009 | Maes et al. | |
| 2009/0035243 A1 | 2/2009 | Czarnota et al. | |
| 2009/0068132 A1 | 3/2009 | Bratescu et al. | |

(Continued)

FOREIGN PATENT DOCUMENTS

DE    2311346 A1    10/1973

(Continued)

OTHER PUBLICATIONS

Maugard, Thierry and Legoy, Marie Dominique; "Enzymatic Synthesis of Derivatives of Vitamin A in Organic Media"; Journal of Molecular Catalysis B: Enzymatic 8; 2000; pp. 275-280.

(Continued)

*Primary Examiner* — Karl J Puttlitz
(74) *Attorney, Agent, or Firm* — Jennifer R. Knight; Michael K. Carrier

(57) ABSTRACT

Retinyl hydroxyesters and retinyl oligo-hydroxyesters were prepared using a chemoenzymatic process from retinol and short chain esters of hydroxycarboxylic acids or short chain esters of hydroxycarboxylic acids. The presence of the hydroxyl group on the acid can result in a mixture of esters from various oligomers of the hydroxycarboxylic acid. The retinyl ester products are readily enzymatically hydrolyzed in vitro, which indicates that application to the skin should result in release of the anti-aging ingredient retinol (without the inherent instability and irritation) along with the acid, which, if chosen appropriately, should also have desirable biological effects. This combination should be effective as an anti-aging skin care ingredient.

12 Claims, 1 Drawing Sheet

U.S. PATENT DOCUMENTS

| | | | |
|---|---|---|---|
| 2010/0035986 A1* | 2/2010 | Maeda et al. | 514/529 |
| 2012/0029198 A1 | 2/2012 | Deng et al. | |

FOREIGN PATENT DOCUMENTS

| | | | |
|---|---|---|---|
| DE | 4415204 A1 | 11/1995 | |
| EP | 0342055 A1 | 11/1989 | |
| EP | 1498104 A1 | 1/2005 | |
| EP | 2072494 A1 | 6/2009 | |
| ES | 2233208 A1 | 6/2005 | |
| ES | 2246603 A1 | 2/2006 | |
| FR | 2 423 602 A1 | 4/1980 | |
| FR | 2919800 A1 | 2/2009 | |
| JP | 2002/193752 A | 7/2002 | |
| JP | 2005 041871 A | 2/2005 | |
| WO | 95/16659 A1 | 6/1995 | |
| WO | 97/20812 A1 | 6/1997 | |
| WO | 02/055540 A1 | 7/2002 | |
| WO | 2004/054992 A1 | 7/2004 | |
| WO | 2005/019156 A2 | 3/2005 | |
| WO | 2005/108534 A1 | 11/2005 | |
| WO | 2007/053794 A2 | 5/2007 | |
| WO | 2009/018389 A1 | 2/2009 | |
| WO | 2009/156324 A2 | 12/2009 | |
| WO | 2011/041487 A1 | 4/2011 | |

OTHER PUBLICATIONS

Maugard, Thierry et al; "Study of Vitamin Ester Synthesis by Lipase-Catalyzed Transesterification in Organic Media"; Biotechnol. Prog.; 2000; vol. 16; pp. 358-362.

Maugard, Thierry et al; "Synthesis of Water-Soluble Retinol Derivatives by Enzymatic Method"; Biotechnol. Prog.; 2002; vol. 18; pp. 424-428.

O'Connor, Charmian J. et al; "*Candida cylindracea* Lipase-Catalysed Synthesis of Retinyl and Oleyl Palmitates; Carbon ChainLength Dependence of Esterase Activity"; Aust. J. Chem.; 1992; vol. 45; pp. 641-649.

Stryer, Lubert; "Acetoacetate is a Major Fuel in Some Tissues"; Biochemistry, Fourth Edition; 1995; Chapter 24, p. 613.

Maugard, T., et al: "Study of Vitamin Ester Synthesis by Lipase-Catalyzed Transesterification in Organic Media"; Biotechnology Progress, vol. 16, No. 3, (2000), pp. 358-362.

Grasso, Salvatore et al,; Hydroxytyrosol lipophilic analgoues: Enzymatic synthesis, radical scavenging activity and DNA oxidative damage protection; Bioorganic Chemistry, 35, 2007, pp. 137-152.

Trujillo, Mariana et al.; "Lipophilic Hydroxytyrosyl Esters. Antioxidant Activity in Lipid Matrices and Biological Systems." Journal of Agricultural and Food Chemistry, 54, 2006, pp. 3779-3785.

Mateos, Raquel, et al.; "New Lipophilic Tyrosyl Esters. Comparative Antioxidant Evaluation with Hydroxytyrosyl Esters"; Journal of Agricultural and Food Chemistry, 56, 2008, pp. 10960-10966.

Gordon, Michael H. et al.; "Antioxidant Activity of Hydroxytyrosol Acetate Compared with That of Other Olive Oil Polyphenols"; Journal of Agricultural and Food Chemistry, 49, 2001, pp. 2480-2485.

Buisman, G. J. H. et al.; "Enzymatic esterifications of functionalized phenols for the synthesis of lipophilic antioxidants"; Biotechnology Letters, vol. 20, No. 2, 1998, pp. 131-136.

Chankeshwara, Sunay V., et al., "Organocatalytic Methods for Chemoselective O-tert-Butoxycarbonylation of Phenols and Their Regeneration from the O-t-Box Derivatives", The Journal of Organic Chemistry, vol. 73, No. 21 (2008), pp. 8615-8618.

Kittisak, Likhitwitayawuid, et al., "Structure Modification of Oxyresveratol for tyrosinase inhibitory activity", Researches Assisted by the Asahi Glass Foundation, Reports, XX, JP, (2008) p. 60. (Abstract).

Charvat, Trevor T., et al., "Design, synthesis, and biological evaluation of chicoric acid analogs as inhibitors of HIV-1 integrase", Bioorganic & Medicinal Chemistry 14 (2006) pp. 4552-4567.

Bratt, Mark O., et al., "Synthesis of Carbonates and Related Compounds from Carbon Dioxide via Methanesulfonyl Carbonates", Journal of Organic Chemistry, American Chemical Society, Easton.; US, vol. 68, No. 14, (2003), pp. 5439-5444.

Dikusar, E. A., et al., "Methyl-and Ethyl Carbonates Derived from Vanillin and Vanillal in the Synthesis of Nitrogen-containing Compounds", Russian Journal of General Chemistry, vol. 77, No. 5, (2007), pp. 905-910.

Jones, Ryan M., et al., "Rapid Syntheses of Benzopyrans from o-OBOC Salicylaldehydes and Salicyl alcohols: A Three-Component Reaction", The Journal of Organic Chemistry, vol. 67, No. 20, (2002), pp. 6911-6915.

Carafa, Marianna, et al., "Superbase-promoted direct N-carbonylation of pyrrole with carbonic acid diesters", Tetrahedron Letters, Elsevier, Amsterdam, NL, vol. 49, No. 22, (2008), pp. 3691-3696.

Hirakawa, Takuya, et al., "A Magentically Separable Heterogeneous Deallylation Catalyst: [CpRu($n^3$-$C_3H_5$)(2-pyridinecarboxylato)]$PF_6$ Complex Supported on a Ferromagnetic Microsize Particle $Fe_3O_4$@$SiO_2$", European Journal of Organic Chemistry, vol. 2009, No. 6, (2009), pp. 789-792.

Hallman, Kristina, et al., "Enantioselective allylic alkylation using polymer-supported palladium catalysts", Tetrahedron: Asymmetry, vol. 10, No. 20, (1999), pp. 4037-4046.

Ouchi, Hidekazu, et al., "1-tert-Butoxy-2-tert-butoxycarbony1-1,2-dihydroisoquinoline: A Novel and Chemoselective tert-Butoxycarbonylation Reagent", Organic Letters, vol. 4, No. 4 (2002), pp. 585-587.

Cuny, Gregory D., et al., "Solution-Phase Ring Opening Cross-Metathesis of Bicyclic Alkenes with Styrene Derivatives and Its Application to "Resin Capture" Solid-Phase Synthesis", Tetrahedron, Elsevier Science Publishers, Amsterdam, NL, vol. 55, No. 27, (1999), pp. 8169-8178.

Kim, Sungbum, et al., "Synthesis and in vitro biological activity of retinyl polyhydroxybenzoates, novel hybrid retinoid derivatives." Bioorganic & Medicinal Chemistry Letters 19, (2009), pp. 508-512.

Database Registry [Online], Chemical Abstracts Service, Columbus, Ohio, US; Jun. 8, 2008, XP002676266, Database accession No. 1026294-10-9 abstract.

Co-pending U.S. Appl. No. 12/975,562 filed Dec. 22, 2011; Neil Warren Boaz.

Co-pending U.S. Appl. No. 61/379,929 filed Sep. 3, 2010; Neil Warren Boaz.

Co-pending U.S. Appl. No. 61/368,850 filed Jul. 29, 2012; Liu Deng.

Notification of Transmittal of the International Search report and Written Opinion of the International Searching Authority, or the Declaration with date of mailing Nov. 17, 2011 for International Application No. PCT/US2011/049047.

Notification of Transmittal of the International Search report and Written Opinion of the International Searching Authority, or the Declaration with date of mailing Sep. 23, 2011 for International Application No. PCT/US2011/045303.

Notification of Transmittal of the International Search report and Written Opinion of the International Searching Authority, or the Declaration with date of mailing May 31, 2012 for International Application No. PCT/US2012/025335.

USPTO Office Action dated Dec. 8, 2012 for co-pending U.S. Appl. No. 12/975,562.

USPTO Office Action dated Jun. 25, 2012 for co-pending U.S. Appl. No. 12/975,562.

\* cited by examiner

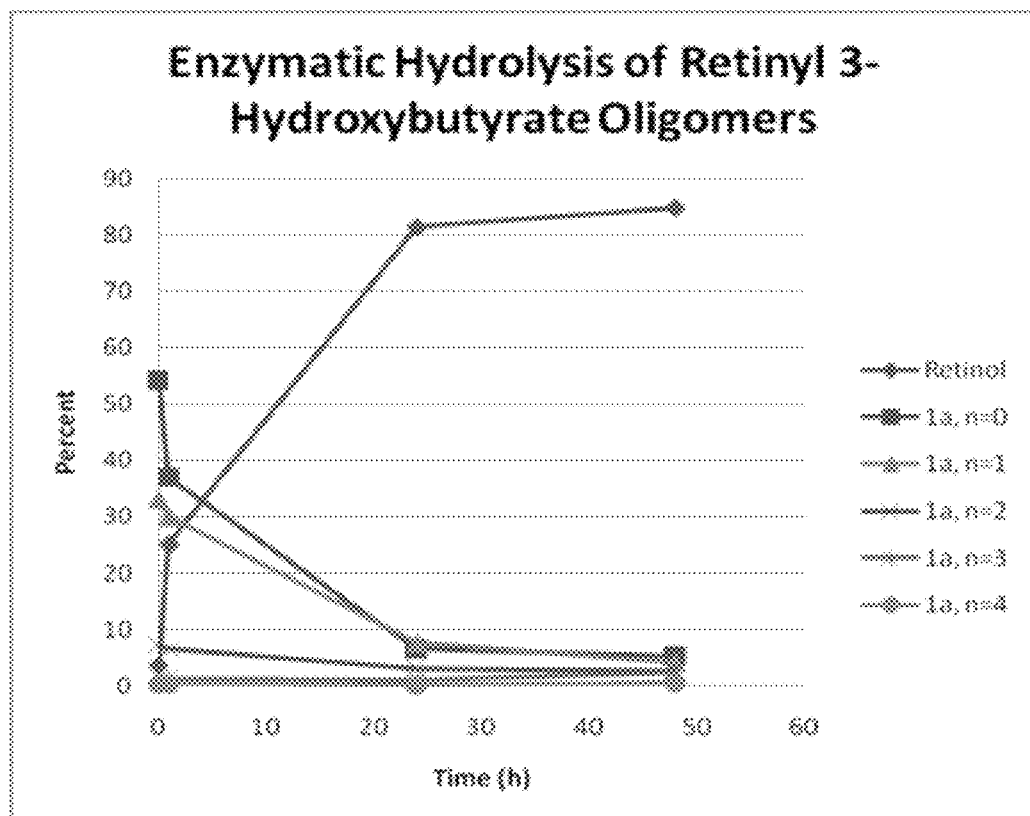

HYDROXYALKANOIC ACID AND HYDROXYALKANOICE ACID OLIGOMER ESTERS OF RETINOL

FIELD OF THE INVENTION

The present invention relates to retinyl esters and to processes for producing them.

SUMMARY OF FIGURES

FIG. 1 shows the extent of enzymatic hydrolysis over time of retinyl 3-hydroxybutyrate oligomers.

BACKGROUND OF THE INVENTION

Retinol (Vitamin A) and its derivatives have a long history as active ingredients in cosmetic compositions to improve the overall appearance of the skin. Retinol itself is unstable and is irritating upon excessive use. Long-chain retinyl esters are therefore sometimes preferred because they are more stable and less irritating to the skin. These esters are expected to be readily hydrolyzed in the skin to afford retinol for metabolism and thus efficacy. Depending on the fatty acid portion of the retinyl ester, the fatty acid hydrolysis product may provide additional benefits. Besides fatty acids, other structures, with various biological properties, are also desired in retinyl conjugates, in order to improve and/or broaden the biological benefits.

Chemical preparation of retinyl esters involves either the reaction of retinol with a long chain acid, acid chloride, or an ester, or by the transesterification of a short-chain retinyl ester with a long-chain fatty acid ester. These processes use either harsh reagents or high temperatures, which can cause degradation due to the instability of the retinol or the retinyl esters to these types of reaction conditions. In addition, these methods are generally incompatible with components having reactive functionalities such as alcohols, unless the alcohols are protected. The protection-deprotection adds cost, time, and waste to the synthesis of these types of molecules.

There have been several reports of biocatalytic syntheses of retinyl esters from retinol (O'Connor et. al. *Aust. J. Chem.* 1992, 45, 641; Maugard, et. al. *J. Mol. Catal. B: Enzymatic* 2000, 8, 275; Maugard et. al., *Biotechnol. Prog.* 2000, 16, 358; Maugard et. al. *Biotechnol. Prog.* 2002, 18, 424.). These methods typically use long-chain acids that facilitate the ester formation and lack complicating reactive groups. An exception is retinyl lactate, which has been prepared by enzymatic esterification of retinol with methyl lactate (Maugard, et. al. *J. Mol. Catal. B: Enzymatic* 2000, 8, 275; Maugard et. al., *Biotechnol. Prog.* 2000, 16, 358; Maugard et. al. *Biotechnol. Prog.* 2002, 18, 424.). This is an unusual case, as the steric hindrance around the hydroxyl group of the lactate renders it relatively unreactive toward enzymatic esterification.

Retinyl esters tend to be more stable and more innocuous than retinol itself. The acid piece can be chosen for these purposes, or can be influenced by other biological considerations. For example, 3-hydroxybutyric acid and esters thereof, including oligomers, are well-known to be cellular energy sources, as noted by Stryer in Biochemistry, 4th edition (1995), p 613, where he states that "Acetoacetate and β-hydroxybutyrate are normal fuels of respiration and are quantitatively important as sources of energy." A coupling of β-hydroxybutyrate or its oligomers with retinol, should it hydrolyze to the constituent acid and alcohol in the cell, could have a double effect—retinol would promote differentiation while the hydroxybutyrate would provide energy.

Thus retinyl esters of 3-hydroxybutyrate and 3-hydroxybutyrate oligomers as well as other hydroxyalkanoates would be novel materials that should be of advantage in cosmetic anti-aging compositions.

SUMMARY OF THE INVENTION

In one aspect, the invention relates to retinyl esters represented by the general formula 1:

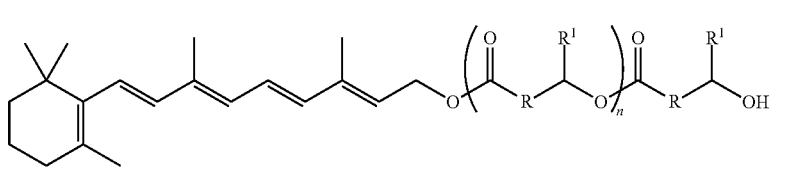

wherein R is selected from substituted and unsubstituted, branched- and straight-chain, saturated, unsaturated, and polyunsaturated divalent $C_1$-$C_{22}$ alkyl, substituted and unsubstituted divalent $C_3$-$C_8$ cycloalkyl, substituted and unsubstituted divalent $C_6$-$C_{20}$ carbocyclic aryl, and substituted and unsubstituted divalent $C_4$-$C_{20}$ heterocyclic wherein the heteroatoms are selected from sulfur, nitrogen, and oxygen; $R^1$ is selected from hydrogen, substituted and unsubstituted, branched- and straight-chain, saturated, unsaturated, and polyunsaturated $C_1$-$C_{22}$ alkyl, substituted and unsubstituted $C_3$-$C_8$ cycloalkyl, substituted and unsubstituted $C_6$-$C_{20}$ carbocyclic aryl, and substituted and unsubstituted $C_4$-$C_{20}$ heterocyclic wherein the heteroatoms are selected from sulfur, nitrogen, and oxygen; and n is 0-10; and mixtures of the foregoing esters.

In another aspect, R is selected from substituted and unsubstituted, branched- and straight-chain, saturated, unsaturated, and polyunsaturated divalent $C_1$-$C_{18}$ alkyl, or a saturated or monounsaturated straight-chain $C_1$-$C_{10}$ alkyl; and $R^1$ is selected from hydrogen, substituted and unsubstituted, branched- and straight-chain, saturated, unsaturated, and polyunsaturated $C_1$-$C_{18}$ alkyl, and n is 0-10.

In another aspect, R is a substituted or unsubstituted, branched- or straight-chain, saturated, unsaturated, or polyunsaturated divalent $C_1$-$C_{10}$ alkyl, or a saturated or monounsaturated straight-chain $C_1$-$C_4$ alkyl; and $R^1$ is hydrogen, a substituted or unsubstituted, branched- or straight-chain, saturated, unsaturated, or polyunsaturated $C_1$-$C_{18}$ alkyl, or $C_1$-$C_{12}$ alkyl, or $C_1$-$C_4$ alkyl; and n is 0-6, or mixtures thereof.

In yet another aspect, R is methyl, ethyl, or propyl; $R^1$ is methyl, ethyl, or propyl; and n is from 0 to 6, or mixtures thereof. In a further aspect, R is methylene; $R^1$ is methyl, and n=1, 2, 3, and 4. That is, the retinyl esters may be a mixture of esters of varying lengths and including repeating units.

In another aspect, the retinyl esters may be derived from retinol and one or more hydroxy-substituted carboxylic acids, for example one or more of 3-hydroxybutyric acid, 3-hydroxy-3-methylbutyric acid, 3-hydroxyoctanoic acid, malic acid, 3-phenyl-3-hydroxypropanoic acid, 10-hydroxydecanoic acid, 12-hydroxydodecanoic acid, 16-hydroxyhexadecanoic acid, or ricinoleic acid.

In another aspect, the esters include oligomers comprised of more than one repeating unit from the one or more hydroxy-substituted carboxylic acids.

In a further aspect, the invention relates to processes for producing the retinyl esters just described, the processes comprising reacting retinol, in the presence of an enzyme, with an acid or short chain ester of a hydroxyalkanoate represented by formula 2

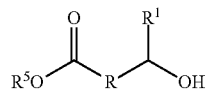

2 wherein R and $R^1$ are as already indicated, and $R^5$ is chosen from hydrogen or $C_1$-$C_5$ straight or branched chain alkane or alkene.

The processes may be carried out in a solvent chosen from diethyl ether, diisopropyl ether, tert-butyl methyl ether, tetrahydrofuran, benzene, toluene, xylene, hexane, heptane, cyclohexane, limonene, dichloromethane, dichloroethane, dibromoethane, tetrachloroethylene, chlorobenzene, acetonitrile, dimethyl formamide, or dimethyl sulfoxide, or mixtures thereof.

In another aspect, the process may be carried out in one or more of toluene, limonene, a heptane, or acetonitrile. Alternatively, the process may be carried out in the absence of a solvent. Enzymes useful according to the process of the invention include one or more of a lipase, an esterase, or a protease, and especially a lipase.

In one aspect, the acid or short chain ester of a hydroxyalkanoate represented by formula 2 may comprise one or more of ethyl 3-hydroxybutyrate or methyl 3-hydroxybutyrate.

In yet another aspect, the invention relates to cosmetic compositions that include the retinyl esters of the invention.

Further aspects of the invention are as disclosed and claimed herein.

DETAILED DESCRIPTION

As used herein, the terms "alkyl" and "alkyl groups" are intended to apply broadly to hydrocarbyl groups without regard to whether the carbons are joined together with a single bond, a double bond, or even a triple bond, so long as the groups contain linked carbon atoms and hydrogen atoms, some of which hydrogen atoms may be substituted by other atoms or groups of atoms, as is well-known in the art of organic chemistry.

Thus, in one aspect, the invention relates to retinyl esters represented by the general formula 1:

wherein R is selected from substituted and unsubstituted, branched- and straight-chain, saturated, unsaturated, and polyunsaturated divalent $C_1$-$C_{22}$ alkyl, substituted and unsubstituted divalent $C_3$-$C_8$ cycloalkyl, substituted and unsubstituted divalent $C_6$-$C_{20}$ carbocyclic aryl, and substituted and unsubstituted divalent $C_4$-$C_{20}$ heterocyclic wherein the heteroatoms are selected from sulfur, nitrogen, and oxygen, and $R^1$ is selected from hydrogen, substituted and unsubstituted, branched- and straight-chain, saturated, unsaturated, and polyunsaturated $C_1$-$C_{22}$ alkyl, substituted and unsubstituted $C_3$-$C_8$ cycloalkyl, substituted and unsubstituted $C_6$-$C_{20}$ carbocyclic aryl, and substituted and unsubstituted $C_4$-$C_{20}$ heterocyclic wherein the heteroatoms are selected from sulfur, nitrogen, and oxygen, and n is 0-10 or mixtures thereof.

The compounds of the invention may be racemic, enantiomerically enriched, diastereomerically enriched, substantially diastereomerically pure, or substantially enantiomerically pure.

In another aspect, the invention relates to species denoted by structures 1 wherein R is selected from substituted and unsubstituted, branched- and straight-chain saturated divalent $C_1$-$C_{18}$ alkyl, substituted and unsubstituted, branched- and straight-chain divalent $C_2$-$C_{18}$ alkenyl, substituted and unsubstituted, branched- and straight-chain divalent $C_4$-$C_{18}$ dienyl, substituted and unsubstituted divalent $C_3$-$C_8$ cycloalkyl, substituted and unsubstituted divalent $C_6$-$C_{12}$ carbocyclic aryl, substituted and unsubstituted divalent $C_4$-$C_{12}$ heterocyclic, $R^1$ is selected from hydrogen, substituted and unsubstituted, branched- and straight-chain saturated $C_1$-$C_{18}$ alkyl, substituted and unsubstituted, branched- and straight-chain $C_2$-$C_{18}$ alkenyl, substituted and unsubstituted, branched- and straight-chain $C_4$-$C_{18}$ dienyl, substituted and unsubstituted $C_3$-$C_8$ cycloalkyl, substituted and unsubstituted $C_6$-$C_{12}$ carbocyclic aryl, substituted and unsubstituted $C_4$-$C_{12}$ heterocyclic, n is 0-6, or mixtures thereof.

The saturated, unsaturated, and polyunsaturated alkyl and cycloalkyl groups which may be represented by R may be straight- or branched-chain divalent hydrocarbon radicals containing up to about 22 carbon atoms and may be substituted, for example, with one to five groups selected from $C_1$-$C_6$-alkoxy, carboxyl, amino, $C_1$-$C_{15}$ aminocarbonyl, $C_1$-$C_{15}$ amido, cyano, $C_2$-$C_6$-alkoxycarbonyl, $C_2$-$C_6$-alkanoyloxy, hydroxy, aryl, heteroaryl, thiol, thioether, $C_2$-$C_{10}$ dialkylamino, $C_3$-$C_{15}$ trialkylammonium and halogen. The terms "$C_1$-$C_6$-alkoxy", "$C_2$-$C_6$-alkoxycarbonyl", and "$C_2$-$C_6$-alkanoyloxy" are used to denote radicals corresponding to the structures —$OR^2$, —$CO_2R^2$, and —$OCOR^2$, respectively, wherein $R^2$ is $C_1$-$C_6$-alkyl or substituted $C_1$-$C_6$-alkyl. The terms "$C_1$-$C_{15}$ aminocarbonyl" and "$C_1$-$C_{15}$ amido" are used to denote radicals corresponding to the structures —NHCOR$^3$, —CONHR$^3$, respectively, wherein $R^3$ is $C_1$-$C_{15}$-alkyl or substituted $C_1$-$C_{15}$-alkyl. The term "$C_3$-$C_8$-cycloalkyl" is used to denote a saturated, carbocyclic hydrocarbon radical having three to eight carbon atoms. The term "halogen" is used to include fluorine, chlorine, bromine, and iodine.

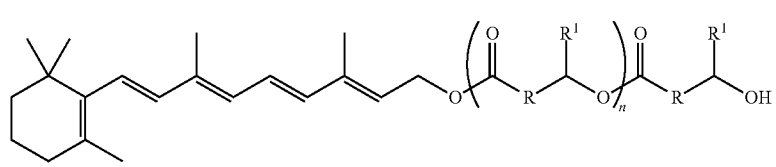

1

The saturated, unsaturated, and polyunsaturated alkyl groups which may be represented by $R^1$ may be straight- or branched-chain hydrocarbon radicals containing up to about 22 carbon atoms and may be substituted, for example, with one to five groups selected from $C_1$-$C_6$-alkoxy, carboxyl, amino, $C_1$-$C_{15}$ aminocarbonyl, $C_1$-$C_{15}$ amido, cyano, $C_2$-$C_6$-alkoxycarbonyl, $C_2$-$C_6$-alkanoyloxy, hydroxy, aryl, heteroaryl, thiol, thioether, $C_2$-$C_{10}$ dialkylamino, $C_3$-$C_{15}$ trialkylammonium and halogen. The terms "$C_1$-$C_6$-alkoxy", "$C_2$-$C_6$-alkoxycarbonyl", and "$C_2$-$C_6$-alkanoyloxy" are used to denote radicals corresponding to the structures —$OR^2$, —$CO_2R^2$, and —$OCOR^2$, respectively, wherein $R^2$ is $C_1$-$C_6$-alkyl or substituted $C_1$-$C_6$-alkyl. The terms "$C_1$-$C_{15}$ aminocarbonyl" and "$C_1$-$C_{15}$ amido" are used to denote radicals corresponding to the structures —$NHCOR^3$, —$CONHR^3$, respectively, wherein $R^3$ is $C_1$-$C_{15}$-alkyl or substituted $C_1$-$C_{15}$-alkyl. The term "$C_3$-$C_8$-cycloalkyl" is used to denote a saturated, carbocyclic hydrocarbon radical having three to eight carbon atoms. The term "halogen" is used to include fluorine, chlorine, bromine, and iodine.

The branching and/or substitution of R and $R^1$ may connect to form a ring.

The aryl groups which R may represent may include divalent phenyl, naphthyl, or anthracenyl and divalent phenyl, naphthyl, or anthracenyl substituted with one to five substituents selected from $C_1$-$C_6$-alkyl, substituted $C_1$-$C_6$-alkyl, $C_6$-$C_{10}$ aryl, substituted $C_6$-$C_{10}$ aryl, $C_1$-$C_6$-alkoxy, halogen, carboxy, cyano, $C_1$-$C_6$-alkanoyloxy, $C_1$-$C_6$-alkylthio, $C_1$-$C_6$-alkylsulfonyl, trifluoromethyl, hydroxy, $C_2$-$C_6$-alkoxycarbonyl, $C_2$-$C_6$-alkanoylamino and 613 $OR^4$, —$S$—$R^4$, —$SO_2$—$R^4$, —$NHSO_2R^4$ and —$NHCO_2R^4$, wherein $R^4$ is phenyl, naphthyl, or phenyl or naphthyl substituted with one to three groups selected from $C_1$-$C_6$-alkyl, $C_6$-$C_{10}$ aryl, $C_1$-$C_6$-alkoxy and halogen. The term "halogen" is used to include fluorine, chlorine, bromine, and iodine.

benzothiazolyl, benzimidazolyl, indolyl and the like. The heterocyclic radicals may be substituted, for example, with up to three groups such as $C_1$-$C_6$-alkyl, $C_1$-$C_6$-alkoxy, substituted $C_1$-$C_6$-alkyl, halogen, $C_1$-$C_6$-alkylthio, aryl, arylthio, aryloxy, $C_2$-$C_6$-alkoxycarbonyl and $C_2$-$C_6$-alkanoylamino. The heterocyclic radicals also may be substituted with a fused ring system, e.g., a benzo or naphtho residue, which may be unsubstituted or substituted, for example, with up to three of the groups set forth in the preceding sentence. The term "halogen" is used to include fluorine, chlorine, bromine, and iodine.

The heterocyclic groups which $R^1$ may represent (or any heteroaryl substituents) include 5- or 6-membered ring containing one to three heteroatoms selected from oxygen, sulfur and nitrogen. Examples of such heterocyclic groups are pyranyl, oxopyranyl, dihydropyranyl, oxodihydropyranyl, tetrahydropyranyl, thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, indolyl and the like. The heterocyclic radicals may be substituted, for example, with up to three groups such as $C_1$-$C_6$-alkyl, $C_1$-$C_6$-alkoxy, substituted $C_1$-$C_6$-alkyl, halogen, $C_1$-$C_6$-alkylthio, aryl, arylthio, aryloxy, $C_2$-$C_6$-alkoxycarbonyl and $C_2$-$C_6$-alkanoylamino. The heterocyclic radicals also may be substituted with a fused ring system, e.g., a benzo or naphtho residue, which may be unsubstituted or substituted, for example, with up to three of the groups set forth in the preceding sentence. The term "halogen" is used to include fluorine, chlorine, bromine, and iodine.

Examples of the compounds of the invention include those represented by formula 1 wherein R is methylene, $R^1$ is methyl and n is from 0 to 6, and mixtures thereof.

In another aspect, the invention relates to retinyl esters represented by the general formula 1:

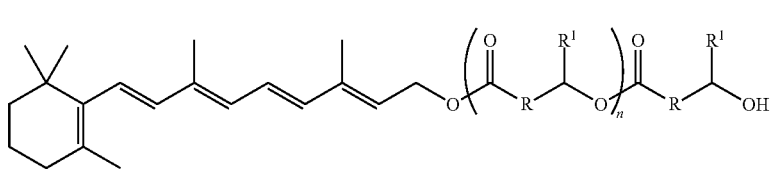

1

The aryl groups which $R^1$ may represent (or any aryl substituents) may include phenyl, naphthyl, or anthracenyl and phenyl, naphthyl, or anthracenyl substituted with one to five substituents selected from $C_1$-$C_6$-alkyl, substituted $C_1$-$C_6$-alkyl, $C_6$-$C_{10}$ aryl, substituted $C_6$-$C_{10}$ aryl, $C_1$-$C_6$-alkoxy, halogen, carboxy, cyano, $C_1$-$C_6$-alkanoyloxy, $C_1$-$C_6$-alkylthio, $C_1$-$C_6$-alkylsulfonyl, trifluoromethyl, hydroxy, $C_2$-$C_6$-alkoxycarbonyl, $C_2$-$C_6$-alkanoylamino and —$OR^4$, —$S$—$R^4$, —$SO_2$—$R^4$, —$NHSO_2R^4$ and —$NHCO_2R^4$, wherein $R^4$ is phenyl, naphthyl, or phenyl or naphthyl substituted with one to three groups selected from $C_1$-$C_6$-alkyl, $C_6$-$C_{10}$ aryl, $C_1$-$C_6$-alkoxy and halogen. The term "halogen" is used to include fluorine, chlorine, bromine, and iodine.

The divalent heterocyclic groups which R may represent include 5- or 6-membered ring containing one to three heteroatoms selected from oxygen, sulfur and nitrogen. Examples of such heterocyclic groups are pyranyl, oxopyranyl, dihydropyranyl, oxodihydropyranyl, tetrahydropyranyl, thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, wherein R is selected from substituted and unsubstituted, branched- and straight-chain, saturated, unsaturated, and polyunsaturated divalent $C_1$-$C_{18}$ alkyl, or $C_1$-$C_{12}$ alkyl, or $C_1$-$C_{10}$ alkyl, or a saturated or monounsaturated straight-chain $C_1$-$C_{10}$ alkyl, or $C_1$-$C_4$ alkyl; and $R^1$ is selected from hydrogen, substituted and unsubstituted, branched- and straight-chain, saturated, unsaturated, and polyunsaturated $C_1$-$C_{18}$ alkyl, or $C_1$-$C_{12}$ alkyl, or $C_1$-$C_4$ alkyl; and n is 0-10, or 1-6, or 1-4, or mixtures thereof.

In various additional aspects, examples of the compounds of the invention thus include those represented by formula 1 wherein R is methyl, ethyl, or propyl, $R^1$ is methyl, ethyl, or propyl, and n is from 0 to 6, and mixtures thereof. We note that if different hydroxyl-substituted acids are used in the processes according to the invention, each of the R and R1 groups may exist independently of one another, but that if a single hydroxyl-substituted acid is used, each of the defined R and R1 groups will be the same, and the retinyl esters produced may include oligomers having varying lengths, such that the retinyl esters are mixtures of compounds in which n=0, n=1, n=2, n=3, etc. However, when n is defined as 0-6, for example, we do not mean to thereby excludes mixtures which contain compounds in which n=7, n=8, etc., although they will typically be present in minor amounts, if at all.

Other examples of the retinyl esters of the invention thus include compounds and mixtures represented by formula 1 wherein R is methylene, $R^1$ is methyl, and n is from 0 to 6, and mixtures thereof containing compounds in which n=0, n=1, n=2, n=3, and n=4.

In another aspect of the invention, the retinyl esters correspond to the general formula 1:

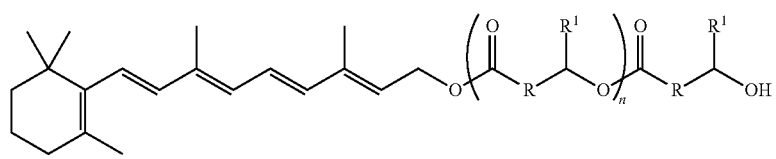

1 wherein R is selected from substituted and unsubstituted, branched- and straight-chain, saturated, unsaturated, and polyunsaturated divalent C1-$C_{2\text{-}2}$ alkyl, or $C_1$-$C_{18}$ alkyl, or $C_1$-$C_{12}$ alkyl, or an unsaturated, monounsaturated, or polyunsaturated straight-chain $C_2$-$C_{22}$ alkyl, or $C_4$-$C_{18}$ alkyl; and $R^1$ is selected from hydrogen, substituted and unsubstituted, branched- and straight-chain, saturated, unsaturated, and polyunsaturated $C_1$-$C_{18}$ alkyl, or $C_1$-$C_{12}$ alkyl, or $C_1$-$C_4$ alkyl; and n is 0-10, or 1-6, or 1-4, or mixtures thereof. In this aspect, the retinyl esters may be derived from retinol and one or more hydroxy-substituted carboxylic acids, for example 3-hydroxybutyric acid, 3-hydroxy-3-methylbutyric acid, 3-hydroxyoctanoic acid, malic acid, 3-hydroxy-3-methylglutaric acid, 3-phenyl-3-hydroxypropanoic acid, 10-hydroxydecanoic acid, 12-hydroxydodecanoic acid, 16-hydroxyhexadecanoic acid, or ricinoleic acid.

The retinyl esters produced from these hydroxyl-substituted acids may include oligomers comprised of more than one repeating unit from the fatty acid, depending upon the reactivity of the hydroxyl-substituted portion of the acid.

Another embodiment of our invention is a novel enzymatic process for the preparation of retinyl ester compounds represented by the general formula 1:

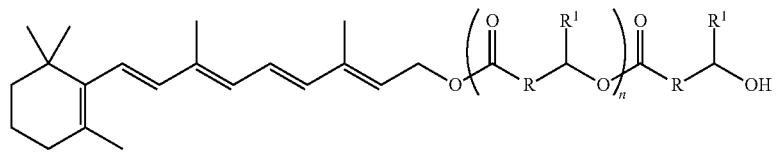

1 wherein,

R is selected from substituted and unsubstituted, branched- and straight-chain, saturated, unsaturated, and polyunsaturated divalent $C_1$-$C_{22}$ alkyl, substituted and unsubstituted divalent $C_3$-$C_8$ cycloalkyl, substituted and unsubstituted divalent $C_6$-$C_{20}$ carbocyclic aryl, and substituted and unsubstituted divalent $C_4$-$C_{20}$ heterocyclic wherein the heteroatoms are selected from sulfur, nitrogen, and oxygen, and $R^1$ is selected from hydrogen, substituted and unsubstituted, branched- and straight-chain, saturated, unsaturated, and polyunsaturated $C_1$-$C_{22}$ alkyl, substituted and unsubstituted $C_3$-$C_8$ cycloalkyl, substituted and unsubstituted $C_6$-$C_{20}$ carbocyclic aryl, and substituted and unsubstituted $C_4$-$C_{20}$ heterocyclic wherein the heteroatoms are selected from sulfur, nitrogen, and oxygen, the compounds represented by formula 1 may be racemic, enantiomerically enriched, diastereomerically enriched, substantially diastereomerically pure, or substantially enantiomerically pure, and n is 0-10 or mixtures thereof by reaction of retinol with an acid or short chain ester of a hydroxyalkanoate represented by general formula 2

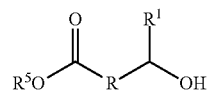

2 wherein R and $R^1$ are as indicated above and $R^5$ is chosen from hydrogen or $C_1$-$C_5$ straight or branched chain alkane or alkene in the presence of a lipase, esterase, or protease.

The process is carried out without solvent or in an inert solvent chosen from cyclic or acyclic ether solvents such as diethyl ether, diisopropyl ether, tert-butyl methyl ether, or tetrahydrofuran, aromatic hydrocarbons such as benzene, toluene, or xylene, aliphatic or alicyclic saturated or unsaturated hydrocarbons such as hexane, heptane, cyclohexane, or limonene, halogenated hydrocarbons such as dichloromethane, dichloroethane, dibromoethane, tetrachloroethylene, or chlorobenzene, polar aprotic solvents such as acetonitrile, dimethyl formamide, or dimethyl sulfoxide, or mixtures thereof.

The preferred solvents are no solvent, toluene, limonene, heptanes, and acetonitrile. The process may be carried out at a temperature between about −100° C. and the boiling point of the solvent, preferably about 0-60° C., most preferably 20-50° C. The amount of acid or short-chain ester 2 may be between 0.85 and 20 equivalents based on retinol, and is preferably between 1 and 10 equivalents, most preferably between 1 and 4 equivalents.

The enzyme used in the process may be chosen from a variety of hydrolytic enzymes, for example a protease, a lipase, or an esterase. Preferred enzymes include lipases. These lipases may be in the form of whole cells, isolated native enzymes, or immobilized on supports.

Examples of suitable lipases include, but are not limited to, Lipase PS (from *Pseudomonas* sp), Lipase PS-C (from *Psue-*

*domonas* sp immobilized on ceramic), Lipase PS-D (from *Pseudomonas* sp immobilized on diatomaceous earth), Lipoprime 50T, Lipozyme TL IM, or Novozym 435 (*Candida antarctica* lipase B immobilized on acrylic resin). Removal of the water or alcohol byproducts, if desired, can be done chemically via a water or alcohol absorbent (e.g., molecular sieves) or by physical removal of the water or alcohol. This by-product removal is preferably done by evaporation, either by purging the reaction mixture with an inert gas such as nitrogen, argon, or helium, or by performing the reaction at reduced pressures, or both, as these conditions can afford >95% conversion of retinol to 1. The preferred pressure for the reaction is between 1 torr and ambient pressure, more preferable between 50 torr and ambient pressure. Any organic solvent that is included in this process may or may not be removed along with the water or alcohol. Examples of 2 include ethyl 3-hydroxybutyrate and methyl 3-hydroxybutyrate.

The product 1 of the process may be isolated using methods known to those of skill in the art, e.g., by extraction, filtration, or crystallization.

The retinyl esters according to the present invention can be used in compositions, such as cosmetic compositions, skin care compositions and the like. The compositions can be useful, for example, for reducing skin roughness, fine lines, and wrinkles, improving photo-damaged skin, regenerating skin, reducing skin hyper-pigmentation, and reducing irritation and/or inflammatory reaction in skin.

Typical cosmetic and/or skin care compositions of the invention contain at least 0.001% by weight of the carbonates according to the present invention. For example, the compositions can contain from about 0.001% to about 20.0% by weight or from about 0.01% to about 10.0% by weight of the retinyl ester according to the present invention. Lower concentrations may be employed for less pronounced conditions, and higher concentrations may be employed with more acute conditions. Suggested ranges also depend upon any adjunct ingredients employed in the compositions.

The cosmetic and skin care compositions of the invention may also contain other skin conditioning ingredients in addition to retinyl esters. Such compositions may include, but are not limited to, skin care ingredients such as retinol, retinyl fatty acid esters, tetronic acid, tetronic acid derivatives, hydroquinone, kojic acid, gallic acid, arbutin, α-hydroxy acids, ascorbic acid and fatty acid esters of ascorbic acid. Such other ingredients are known to those of skill in the art.

Typically, topical application to skin sites is accomplished in association with a carrier. Where employed, the carrier is desirably inert in the sense of not bringing about a deactivation or oxidation of active or adjunct ingredient(s), and in the sense of not bringing about any significant adverse effect on the skin areas to which it is applied. For example, the compounds according to the present invention may be applied in admixture with a dermatologically acceptable carrier or vehicle (e.g., as a lotion, cream, ointment, soap, stick, or the like) so as to facilitate topical application and, in some cases, provide additional beneficial effects as might be brought about, e.g., by moisturizing of the affected skin areas.

Suitable preparations include lotions containing oils and/or alcohols and emollients such as olive oil, hydrocarbon oils and waxes, silicone oils, other vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids.

The novel processes provided by the present invention are further illustrated by the following examples.

EXAMPLES

Example 1

Preparation of Retinyl 3-Hydroxybutyrate (1a) Oligomers (n=0-4)

To a vial was added retinol in heptane (58% retinol; 25.9 g; 15.0 g retinol; 52.4 mmol), ethyl 3-hydroxybutyrate (20.76 g; 157 mmol; 3 equiv), and Novozym 435 (1.5 g). The mixture was stirred at room temperature and purged with a stream of nitrogen through the mixture for 48 h to afford 96.7% conversion of retinol to a mixture of retinyl 3-hydroxybutyrate oligomers. The mixture was diluted with toluene (30 mL), filtered and the solid was washed with toluene (30 mL). The toluene solution was washed with 1:1 water:methanol (60 mL) and the aqueous decant was back-extracted with heptanes (25 mL). The combined organic layer was washed with 1:1 water:methanol (60 mL), dried with sodium sulfate, and concentrated to afford 17.79 g of 1a (R═CH$_2$, R$^1$═CH$_3$) as a thick yellow oil. HPLC analysis indicated 3.7% retinol and 95.5% 1a oligomers. The proportion by HPLC is 1a, n=0 (53.7%), 1a, n=1 (32.9%), 1a, n=2 (7.1%), 1a, n=3 (1.4%), and 1a, n=4 (0.3%).

HPLC and HPLC-MS (4.6×150 mm Zorbax SB-C8 column [Agilent], 3.5μ thickness, 80:20 methanol:water (containing 0.1% trifluoroacetic acid) for 20 min, detection at 325 nm): $t_R$ 6.6 min (retinol); $t_R$ 8.0 min (1a, n=0, M$^+$=372); $t_R$ 8.8 min (1a, n=1, M$^+$=458); $t_R$ 9.7 min (1a, n=2, M$^+$=544); $t_R$ 10.6 min (1a, n=3, M$^+$=630); $t_R$ 11.8 min (1a, n=4, M$^+$=716).

Example 2

Preparation of Retinyl Ricinoleate (1b)

To a vial was added retinol in toluene (54% retinol; 1.852 g; 1.0 g retinol; 3.49 mmol), ricinoleic acid (80%; 1.250 g; 4.19 mmol; 1.2 equiv), and Novozym 435 (1 g). The mixture was sealed and stirred at room temperature for 21 h to afford 83% conversion of retinol to 1b.

HPLC (4.6×150 mm Zorbax SB-C8 column [Agilent], 3.5μ thickness, 90:10 methanol:water (containing 0.1% trifluoroacetic acid) for 7 min, gradient to 95:5 methanol:water (containing 0.1% trifluoroacetic acid) over 1 min, hold for 12 min, gradient to 100% methanol over 1 min, hold at 100% methanol, detection at 325 nm): $t_R$ 3.9 min (retinol); $t_R$ 14.2 min (1b).

Example 3

Enzymatic Hydrolysis of Retinyl 3-Hydroxybutyrate (1a) oligomers (n=0-4)

Retinyl 3-hydroxybutyrate oligomers (1a; 100 mg) was dissolved in 2 mL of toluene. pH 7 Buffer (2 mL) was added. Novozym 435 (100 mg) was added, and the mixture was stirred vigorously at ambient temperature. The top layer was sampled at 1, 24, and 48 h and analyzed by HPLC. The results are shown in FIG. 1, and indicate significant hydrolysis to retinol over 48 h. A control reaction without enzyme showed no hydrolysis after 48 h.

That which is claimed is:

1. Retinyl esters represented by the general formula 1:

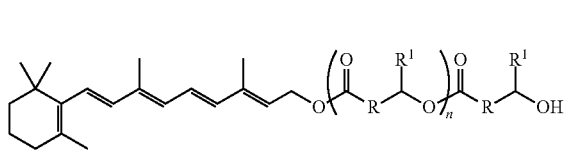

wherein,
R is methylene, ethylene, or propylene; R1 is methyl, ethyl, or propyl; and n is from 0 to 6, or mixtures thereof.

2. The retinyl esters of claim 1, wherein R is methylene; $R^1$ is methyl, and n=0, 1, 2, 3, and 4.

3. Retinyl esters represented by formula 1:

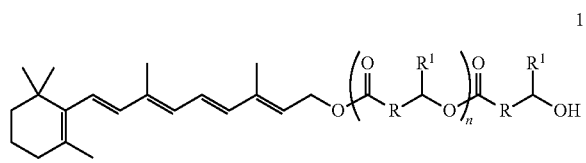

wherein the retinyl esters are derived from retinol and one or more hydroxy-substituted carboxylic acids selected from the group consisting of 3-hydroxybutyric acid, 3-hydroxy-3-methylbutyric acid, 3-hydroxyoctanoic acid, malic acid, 3-hydroxy-3-methylglutaric acid, 3-phenyl-3-hydroxypropanoic acid, 10-hydroxydecanoic acid, 12-hydroxydodecanoic acid, 16-hydroxyhexadecanoic acid, and ricinoleic acid; and n is 0 - 10.

4. The retinyl esters of claim 3, wherein the esters include oligomers comprised of more than one repeating unit from the one or more hydroxy-substituted carboxylic acids.

5. A process for producing the retinyl esters of claim 1, the process comprising reacting retinol, in the presence of an enzyme, with an acid or short chain ester of a hydroxyalkanoate represented by formula 2

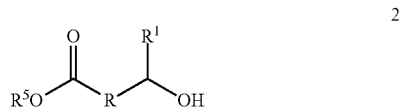

wherein R and $R^1$ are as indicated in claim 1, and $R^5$ is chosen from hydrogen or $C_1$-$C_5$ straight or branched chain alkane or alkene.

6. The process of claim 5, wherein the process is carried out in a solvent selected from one or more of the group consisting of diethyl ether, diisopropyl ether, tert-butyl methyl ether, tetrahydrofuran, benzene, toluene, xylene, hexane, heptane, cyclohexane, limonene, dichloromethane, dichloroethane, dibromoethane, tetrachloroethylene, chlorobenzene, acetonitrile, dimethyl formamide, and dimethyl sulfoxide.

7. The process of claim 5, wherein the solvent is selected from one or more of the group consisting of toluene, limonene, heptane, and acetonitrile.

8. The process of claim 5, wherein the process is carried out in the absence of a solvent.

9. The process of claim 5, wherein the enzyme comprises one or more of a lipase, an esterase, or a protease.

10. The process of claim 5, wherein the enzyme is a lipase.

11. The process of claim 5, wherein the acid or short chain ester of a hydroxyalkanoate represented by formula 2 comprises one or more of ethyl 3-hydroxybutyrate, methyl 3-hydroxybutyrate, or ricinoleic acid.

12. A cosmetic composition comprising the retinyl esters of claim 1.

* * * * *